United States Patent
Cummins et al.

(10) Patent No.: US 10,383,675 B1
(45) Date of Patent: Aug. 20, 2019

(54) SCREW RETENTION SLEEVE

(71) Applicant: Zavation, LLC, Flowood, MS (US)

(72) Inventors: John Franklin Cummins, Kosciusko, MS (US); John Lawrence Walker, Madison, MS (US); Joseph Matthew Jones, Madison, MS (US)

(73) Assignee: ZAVATION, LLC, Flowood, MS (US)

( * ) Notice: Subject to any disclaimer, the term of this patent is extended or adjusted under 35 U.S.C. 154(b) by 0 days.

(21) Appl. No.: 16/135,573

(22) Filed: Sep. 19, 2018

Related U.S. Application Data (60) Provisional application No. 62/727,493, filed on Sep. 5, 2018.

(51) Int. Cl.
  *A61B 17/88* (2006.01)
  *B25B 23/10* (2006.01)

(52) U.S. Cl.
  CPC ...... *A61B 17/8886* (2013.01); *A61B 17/8891* (2013.01); *B25B 23/10* (2013.01); *B25B 23/101* (2013.01); *B25B 23/103* (2013.01)

(58) Field of Classification Search
  CPC ............ A61B 17/8891; A61B 17/8888; A61B 17/8886; A61B 17/0401; A61B 17/8047; B25B 23/101; B25B 23/10; B25B 23/02; B25B 23/105; B25B 23/103; B25B 23/106; B25B 23/108
  USPC ............................................. 606/104; 81/453
  See application file for complete search history.

(56) References Cited

U.S. PATENT DOCUMENTS

| | | | |
|---|---|---|---|
| 6,149,653 A * | 11/2000 | Deslauriers | A61B 17/0401 606/232 |
| 9,078,717 B2 | 7/2015 | Griffiths et al. | |
| 9,402,662 B2 | 8/2016 | Mahar | |
| 2008/0020091 A1 | 1/2008 | Rossin | |
| 2009/0062862 A1* | 3/2009 | Perrow | A61B 17/8047 606/280 |
| 2014/0311303 A1* | 10/2014 | Lin | B25B 23/101 81/452 |
| 2016/0082576 A1* | 3/2016 | Pamatmat | B25B 23/10 81/453 |

* cited by examiner

*Primary Examiner* — Eric S Gibson
*Assistant Examiner* — Marcela I Shirsat
(74) *Attorney, Agent, or Firm* — Olive Law Group, PLLC (57) ABSTRACT

A surgical screw driving device for driving a screw into a surgical fixture. The device has a screwdriver having a proximal end, a distal end having a driver for engaging the screw, and an elongated shaft extending therebetween. The device has a screw retainer surrounding and extending along the elongated shaft. The screw retainer is configured to engage and hold a periphery of a screw head prior to the screw being driven into the surgical fixture. The screw retainer is configured to disengage from the periphery of the screw head as an axial end of the screw retainer contacts the surgical fixture and is further configured, upon disengagement and without necessity of outside assistance, to translate along the elongated shaft of the screwdriver away from the distal end and toward the proximal end.

19 Claims, 12 Drawing Sheets

Once disengaged from the screw head, the sleeve is retained on a taper that is machined on the shaft

SCREW RETENTION SLEEVE

CROSS REFERENCE TO RELATED APPLICATIONS

This application is related and claims priority to U.S. Ser. No. 62/727,493, entitled Screw Retention Sleeve, filed Sep. 5, 2018, the entire contents of which are incorporated herein by reference.

BACKGROUND OF THE INVENTION

Field of Invention

The invention relates to the field of surgical orthopedic tools.

Discussion of the Background

As described in U.S. Pat. Apl. Publ. No. 20080200918, the human spine provides a vast array of functions, many of which are mechanical in nature. The spine is constructed to allow nerves from the brain to pass to various portions of the middle and lower body. These nerves, typically called the spinal cord, are located in a region within the spine called the spinal canal. Various nerve bundles emerge from the spine at different locations along the lateral length of the spine. In a healthy spine, these nerves are protected from damage and/or undue pressure thereon by the structure of the spine itself.

The spine has a complex curvature made up of a plurality of individual vertebrae separated by intervertebral discs. These discs hold the vertebrae together in a flexible manner so as to allow a relative movement between the vertebrae from front to back and from side to side. This movement then allows the body to bend forward and backward, to bend from side to side, and to rotate about a vertical axis. Throughout this movement, when the spine is operating properly the nerves are maintained clear of the hard structure of the spine.

Over time, or because of accidents, the intervertebral discs loose height, become cracked, dehydrated, or herniated. The result is that the disc height is reduced leading to compression of the nerve bundles, causing pain and in some cases damage to the nerves.

Currently, there are many systems and methods at the disposal of a physician for reducing, or eliminating, the pain by minimizing the stress on the nerve bundles. In some instances, the existing disk is removed and an artificial disk is substituted therefore. In other instances, two or more vertebrae are fused together to prevent relative movement between the fused discs.

Often there has been required a system and method for maintaining, or recreating, proper space for the nerve bundles that emerge from the spine at a certain location. In some cases a cage or bone graft is placed in the disc space to preserve, or restore, height and to cause fusion of the vertebral level. As an aid in stabilizing the vertebrae, one or more rods, plates, or braces are placed between the fused vertebrae with the purpose of supporting the vertebrae, while fusion takes place. These rods and/or plates are often held in place by anchors which are fitted into the pedicle of the vertebrae. One type of anchor is a pedicle screw, and such screws come in a variety of lengths, diameters, and thread types.

U.S. Pat. No. 9,078,717 (the entire contents of which are incorporated herein by reference) describes a bone screw driving system which includes a screw having a head and a shaft extending from the head. The screw includes a stepped opening extending in the shaft that includes a first portion and a second portion having a greater cross-sectional dimension than the first portion. The bone screw driving system of the '717 patent further includes a screw driver having a driver shaft that defines a tip configured to engage the screw head. The driver further includes a pin extending from the tip and sized to fit within the opening of the screw to thereby retain the screw.

U.S. Pat. No. 9,402,662 (the entire contents of which are incorporated herein by reference) describes a spinal instrument with a set screw loading and retention mechanism which includes a first tube, a screw slot, and a retention mechanism. The first tube includes an inner lumen disposed concentric and proximate to a head portion of a bone screw. The screw slot is disposed along a portion of the first tube at a distance from the head portion of the bone screw and is configured for loading of a set screw for locking a spinal rod within the head portion of the bone screw. The retention mechanism is disposed along at least a portion of the inner tube configured to selectively retain the set screw.

SUMMARY OF THE INVENTION

In one embodiment, there is provided a surgical screw driving device for driving a screw into a surgical fixture. The device has a screwdriver having a proximal end, a distal end having a driver for engaging the screw, and an elongated shaft extending therebetween. The device has a screw retainer surrounding and extending along the elongated shaft. The screw retainer is configured to engage and hold a periphery of a screw head prior to the screw being driven into the surgical fixture. The screw retainer is configured to disengage from the periphery of the screw head as an axial end of the screw retainer contacts the surgical fixture and is further configured, upon disengagement and without necessity of outside assistance, to translate along the elongated shaft of the screwdriver away from the distal end and toward the proximal end.

In another embodiment, there is provided a method of driving a screw with the surgical screw driving device described above. The method comprises bringing a screw head of the screw to contact with the screw retainer described above, such that the screwdriver becomes engaged with the screw head; moving the screwdriver to a first site of the surgical fixture, such that the screwdriver delivers the screw into drivable contact with the first site; rotating the screwdriver, such that the driver at the distal end of the screwdriver drives the screw until the axial end of the screw retainer comes into contact with the surgical fixture; and further rotating the driver after contact to disengage the screw retainer from the screw head, wherein a translation force is generated by the screw retainer upon disengagement which translates the screw retainer away from the screw head.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

To facilitate fusion of the cervical spine, cervical plate fixation is often used to join the vertebras together and provide stability during the fusion process. A cervical plate is held in place by bone screws installed through the plate and into the vertebras. During the surgical procedure, a surgical technician often loads a screw onto the screwdriver and passes the assembly to the physician upon his request. It is important that the screw remain on the tip driver during the transition from the sterile field to the patient. This has been accomplished in the past using a range of concepts that either rely on the friction of an interference fit (e.g., plastic inserts, split tip drivers, tapered drivers, etc) or physically attaching the screw to the driver (threaded cannula that attaches to the screw, sleeves that encapsulate the screw head, etc).

Friction fit drivers are often unreliable due to incorrect machining or user error during the procedure. Threading the screws onto the driver can lead to weak drivers that often fail after repeated use. Screw retention sleeve are often bulky and impair a physician's view of the implants during installation. Both threaded screws and sleeves require the physician to disengage the driver/sleeve from the screws after installation.

In one embodiment of the invention, the driver device has a sleeve that physically retains the screw to the driver, but with a slimmer profile. In one embodiment of the invention, the sleeve automatically disengages from the screw when installed into the cervical plate. Although there are similar sleeves available on the market, the sleeve of this embodiment of the present invention provides a slimmer profile than conventional ones, automatically disengages from the screw, and self retains itself on the driver.

The self-retention on the driver is one aspect of the invention which sets this sleeve apart from conventional ones. Once the sleeve has retained itself at an upper position on the shaft, the physician is able to use the same driver to turn the screw locks on the plate. In the upper position, the sleeve is not covering the driving element of the driver and the physician can see the driving element engage with the screw locks.

FIGS. 1-12 and their subviews illustrate the use of several exemplary embodiments of the invention comprising a screw retainer sleeve and driver.

Figure 1:
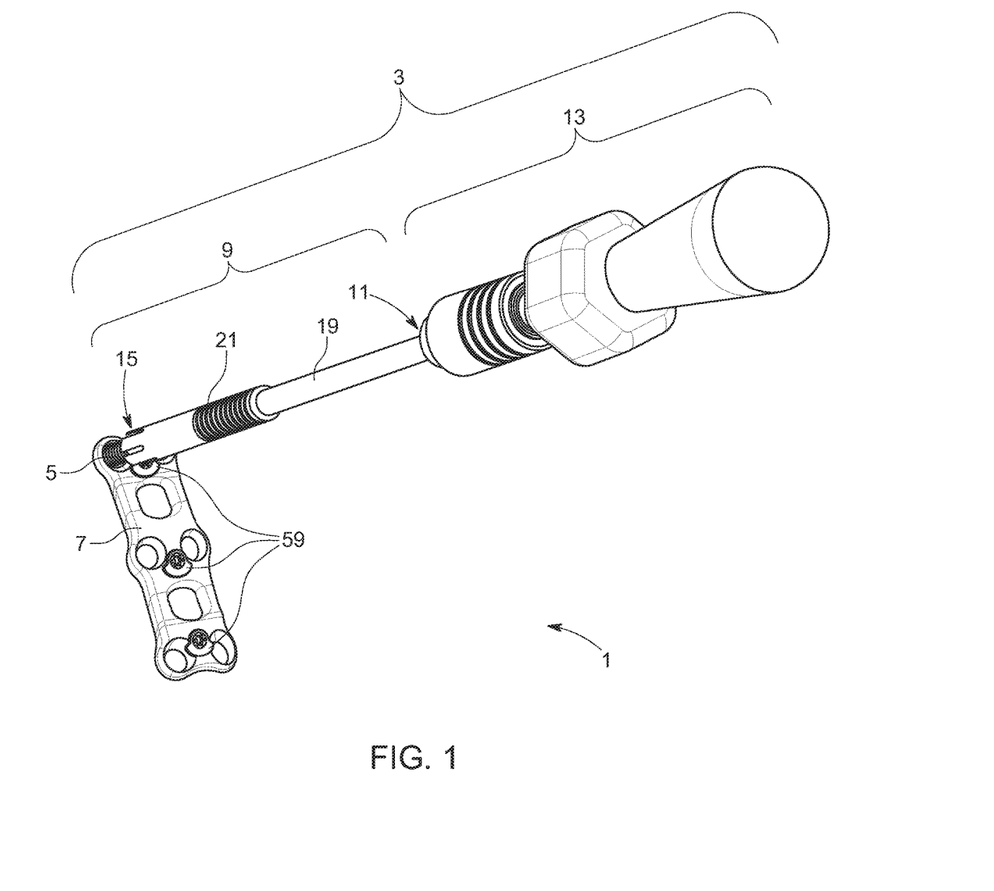
FIG. 1 is a schematic of a surgical screw driving device attaching screws to a surgical fixture.

Referring now to FIG. 1, what is shown in this illustrative and non-limiting embodiment is a surgical kit (1) embodiment of the present invention. It comprises a screw 5, a surgical fixture 7, a screwdriver 9 (having an elongated shaft 19, a proximal end 11 a distal end 15, and a screw retainer sleeve 21), and a handle 13 for coupling to the proximal end 11 of the screwdriver 9, clear of the screw retainer sleeve 21. This figure in particular shows that the screw 5 is retained to the screwdriver 9 with the screw retainer 21 during installation of the screw 5 into the surgical fixture 7. Not visible in FIG. 1 is that the screw 5 is engaged with a driver (17, see FIGS. 2-12 showing different views and other embodiments of the invention) disposed on the distal end 15 of the elongated shaft 19. It is obscured from view in FIG. 1 by the screw retainer sleeve 21.

Referring now to FIGS. 2A-D, what is shown are several views of components of an exemplary screwdriver embodiment of the present invention, in use to drive a screw 5 into a surgical fixture 7. In all of FIGS. 2A-D are an elongated shaft 19, a screw retainer 21, and an axial end 27 of the screw retainer 21.

Figures 2A, 2B, 2C:
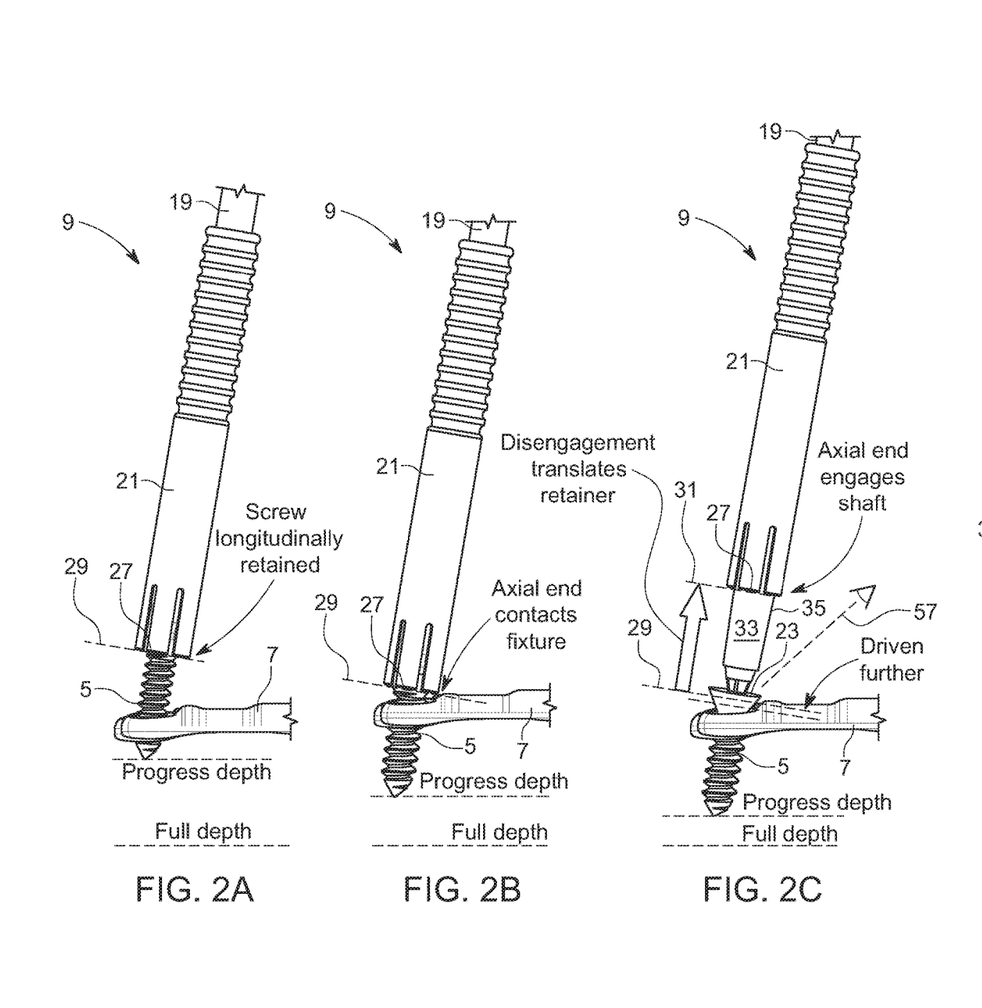
FIGS. 2A-2D are schematics showing the action of the screw retainer as the screw is driven into the fixture.

FIG. 2A shows the screw 5 being delivered to the site of a surgical fixture 7 (and initially driven to a progress depth) by the screw 5 being longitudinally retained with the screw retainer 21. The screw retainer 21 is engaged and retained longitudinally to the elongate shaft 19. The relative position of the retainer 21 to the shaft 19 is a first position 29 of retainment of the screw 5 and retainer 21 to the shaft 19.

FIG. 2B shows the screw 5 being driven to a deeper progress depth. The screw 5 has been driven to a distance at which the axial end 27 has come into contact with the fixture 7, while the retainer 21 and screw 5 are still arranged relative to one another in the first position 29. It comprises a screw 5, a surgical fixture 7, a screwdriver 9 (having an elongate shaft 19, a proximal end 11 a distal end 15, and a screw retainer sleeve 21), and a handle 13 for coupling to the proximal end 11 of the screwdriver 9, clear of the screw retainer 21. This figure in particular shows that the screw 5 is retained to the screwdriver 9 with the screw retainer 21 during installation of the screw 5 into the surgical fixture 7.

FIG. 2C shows the screw 5 having been driven to a slightly deeper progress depth than in FIG. 2B. Here, the further driving has caused the screw retainer 21 to disengage from the screw 5, the disengagement translating the retainer 21 to a second position 31, and without necessity of outside assistance. In this second position 31, there is a clear line of sight 57 to the screw head 23. The line of sight 57 shows that the screw head 23 is engaged with a driver 17.

The driver 17 is disposed at the distal end (15, FIG. 1) of the elongate shaft 19, and below a tapered section 33 of the shaft 19. The tapered section provides a sufficiently large diameter 35 at which the retainer engages the shaft 19 in the second position 31 that the retainer 21 remains retained to the tapered section 33 and the shaft 19 after disengaging from the screw head to translate to the second position 31.

Figure 2D:
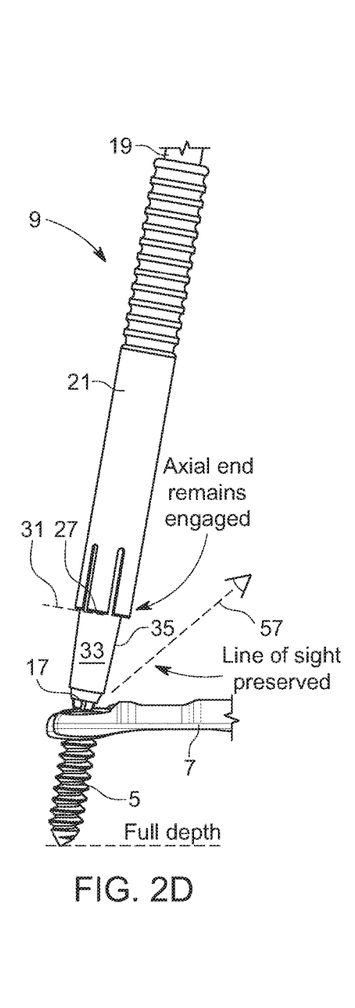
Figure 3A:
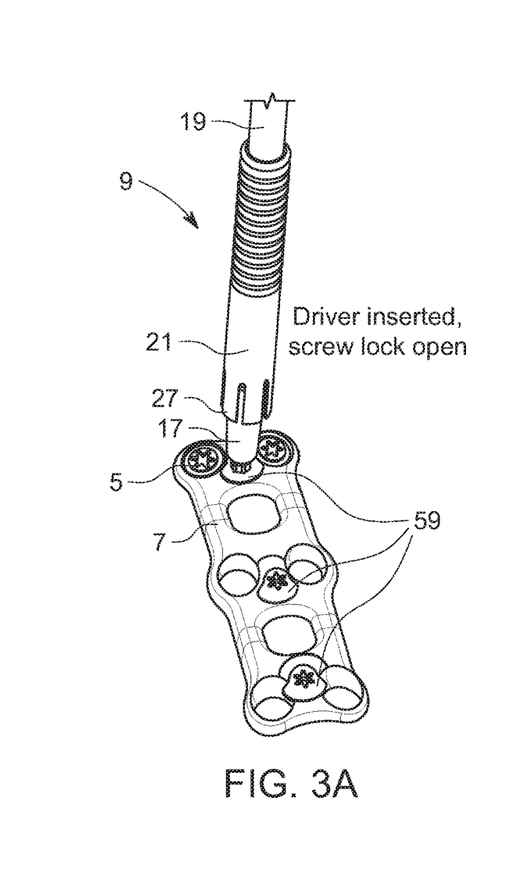
FIG. 3A-3C are schematics showing surgical screw driving device rotating screw locks into place.
Figure 3B:
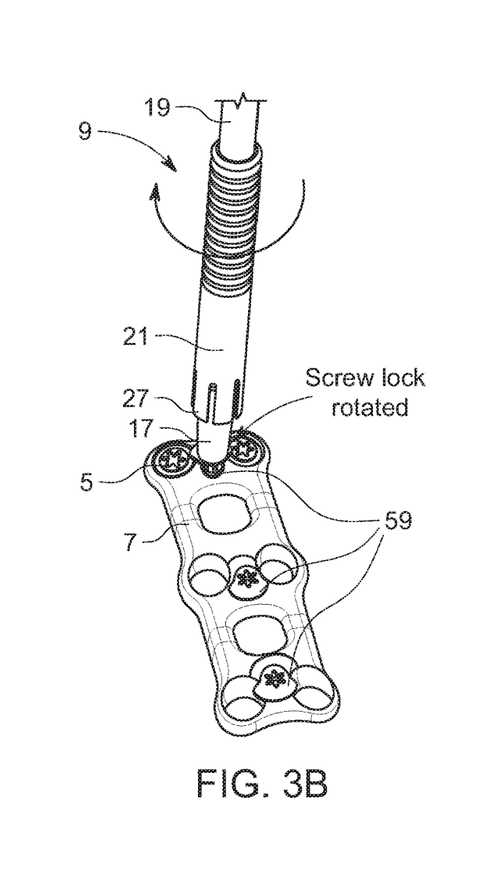
Figure 3C:
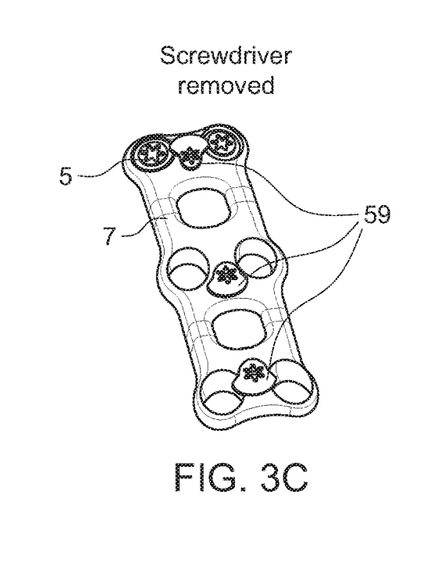

Referring now to FIG. 2D, the screw 5 has been driven completely to its full depth, such that the screw 5 is seated in the surgical fixture 7. The retainer 21 remains engaged with the shaft 19, at the second position 31 (where the axial end 27 is held by the diameter 35), such that the line of slight 57 is preserved without obstruction. In this configuration, the driver 17 is freely able to be removed from the screw 5 by movement of the shaft 19 away from the site of the fixture 7, without any other steps or actions. This embodiment shows that the present invention has provided a device that allows a surgeon or physician to install a screw 5 with the benefit of single-tool screw retainment, and does not require the physician to take any action to disengage the screw 5 and/or retain the retainer sleeve 21 out of his line of sight 57, and/or use a separate tool to set screw locks. Referring now to FIGS. 3A-C, what is shown are several views of an exemplary screwdriver embodiment of the present invention, in use to drive a rotational fastener 59, a screw lock, to lock a screw 5 that has been installed into a surgical fixture 7. The angle shown is representative of a potential line of sight view that a physician would have when using the embodiment.

Referring now to FIGS. 3A and 3B: like the embodiment shown in FIGS. 2C and 2D, the screw retainer sleeve 21 is held with its axial end 27 away from the driver 17. Here, though, the driver 17 has been engaged with the rotational fastener 59, such that the engagement of the driver 17 with the fastener 59, rather than a screw 5. Relative to FIG. 3A, in FIG. 3B, the screwdriver 9 has been rotated such that the fastener 59 has locked the screw 5 against backing out of the fixture 7. In FIG. 3C, the screwdriver 9 has been removed, such that the driver 17 is no longer in contact with the fastener 59.

An advantage of the embodiment shown in FIGS. 3A-C is that the screw retainer sleeve 21 allows a single screwdriver 9 to eliminate the need for additional steps to removing a screwdriver from a site and bring a different tool to the site, to rotate an adjacent fastener, such as the screw locks 59. Typical cervical screws require dedicated tools of with a specific engagement shape to engage and drive the screws, and that specific shape makes those dedicated tools so dissimilar to the shape of adjacent fasteners that additional tools that must be used to rotate such other fasteners (ones such-as or analogous-to the screw locks 59 shown in FIGS. 3A-C).

The screw retainer sleeve 21 allows a part of a screw head that is not of a dedicated engagement shape (for a dedicated tool), a screw head periphery 25 (FIGS. 2C; 5A,B; 6A-D; 7; 9A,B; 10; 12A-F) to be retained to a screwdriver 9 having a driver 17 that may be compatible with a wide variety of conventional fastener, screw, screw lock, or other shapes. Therefore, because it provides screw retainment for a screw 5 having a similar engagement shape to the rotational fastener 59 makes the present invention capable of serving as a single tool that allows directly moving between a screw 5 and rotational fastener 59 at the same site.

Figures 4A, 4B:
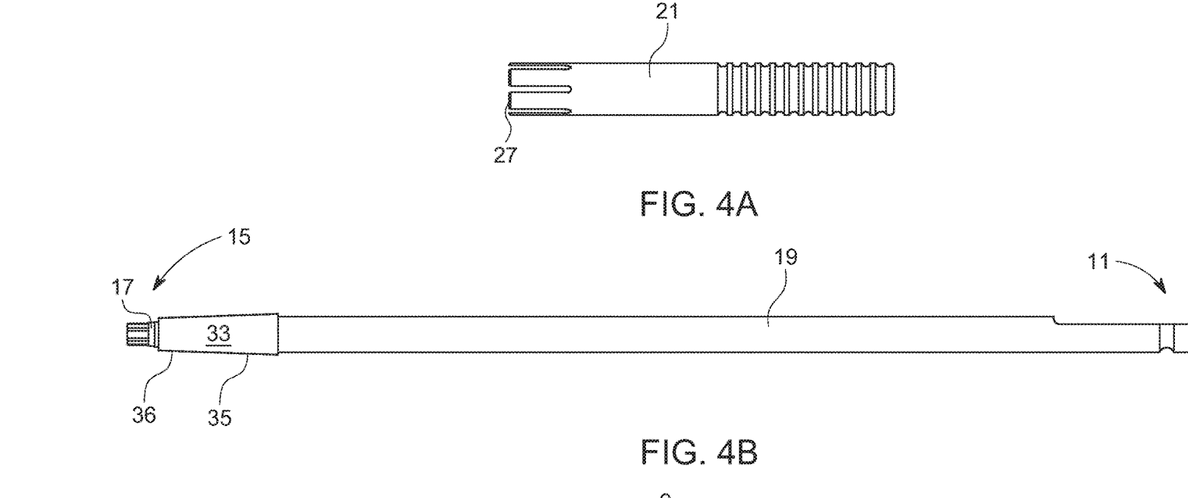
FIGS. 4A-4C are schematics of illustrative components of the surgical screw driving device.
Figure 4C:
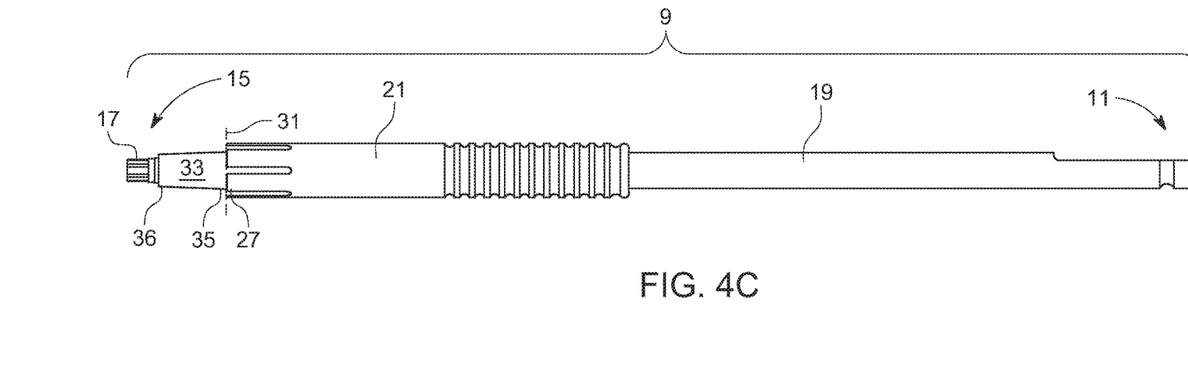

Referring now to FIGS. 4A-C, what is shown are component views of an exemplary embodiment of the present invention and a screwdriver 9 embodiment of the present invention comprising those components. FIG. 4A shows a similar screw retainer sleeve 21 to FIGS. 1-3, and its axial end 27. FIG. 4B shows a similar elongated shaft 19 to FIGS. 1-3, with its proximal end 11, distal end 15, driver 17 disposed at the distal end 15, and the tapered section 33. The tapered section 33 is characterized by having a smaller diameter 36 proximate to the distal end 15 that is smaller than a larger diameter 35 (35, FIGS. 2C-D) which is closer to the proximal end 11. FIG. 4C shows the screw retainer sleeve 21 arranged coaxially on the shaft 19, as components of a screwdriver 9. The axial end 27 is arranged proximate to the larger diameter 35 at the second position 31 (FIGS. 2C-D).

Figure 5A:
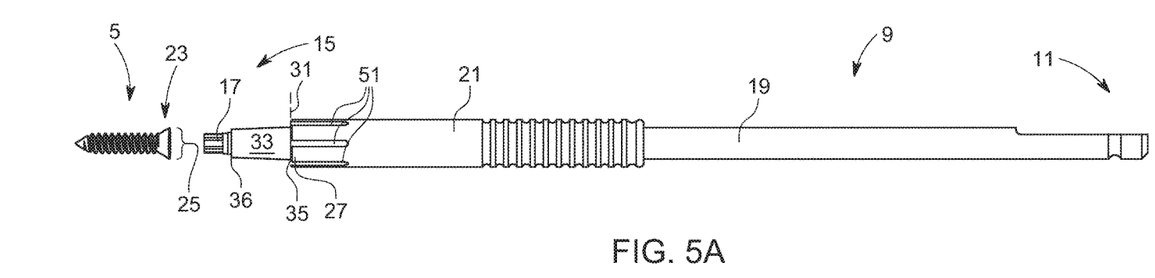
FIGS. 5A-5C are schematics illustrating the engagement of the screw retainer to the screw head.
Figure 5B:
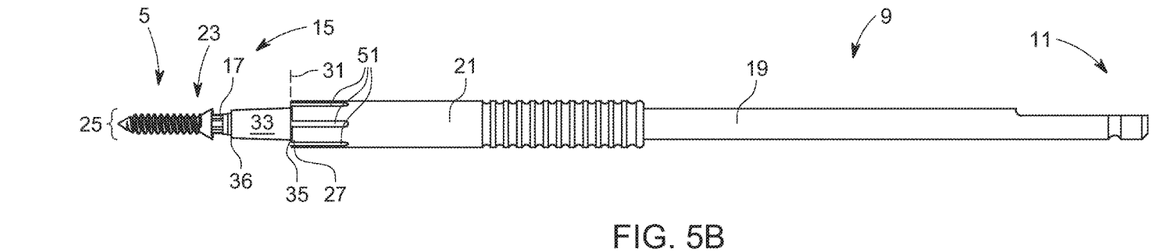
Figure 5C:
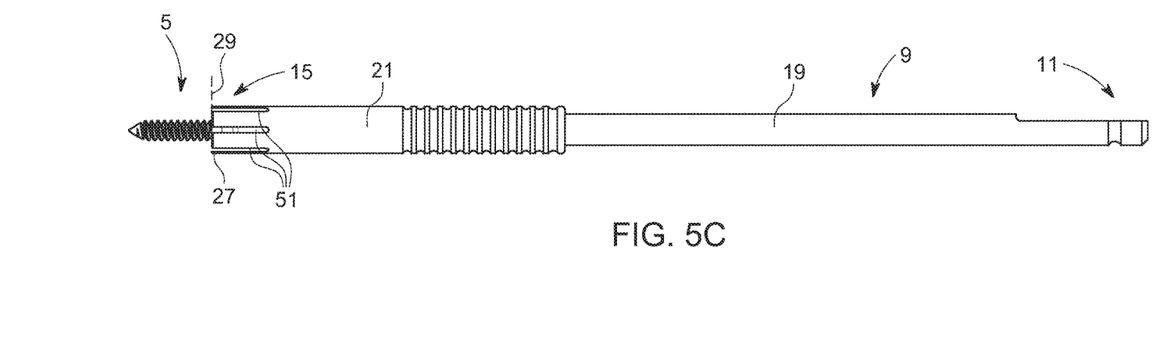

Referring now to FIGS. 5A-C, what is shown are configuration views of engagement of an exemplary screwdriver 9 embodiment of the present invention with a screw 5, which are similar to the embodiment shown in FIG. 4C. The embodiments shown here comprise screw retainer sleeves 21 that have slots 51 arranged at intervals about the circumference of the sleeve 21. These allow the screw retainer to deform to facilitate functioning as a screw retainer 21. In FIG. 5A, the screw 5 is longitudinally aligned with the driver 17, but is not translated into engagement with the driver 17. The screw has a screw head 23 with a periphery 25. In FIG. 5B, the screw head 23 has been translated onto the driver 17 longitudinally, such that the driver 17 is engaged with the screw head 25. In this position, the driver 17 is rotationally and torsionally engaged with the screw head 23.

In FIG. 5C, the screw retainer sleeve 21 has been translated longitudinally relative to the shaft 19, such that the axial end 27 is now in a first position 29, overlapping and engaging with the screw head 23 longitudinally and retaining the screw head 23 longitudinally to the shaft 19, in addition to the driver 17 engaging the screw head 23 and retaining it to the shaft 19 rotationally and torsionally. The slots 51 facilitated this engagement by effecting the axial end 27 with the ability to deform and bend outwardly, radially-outward relative to the shaft 19.

When the sleeve is pushed over the screw head, the slots in the sleeve allow for the end to flare out and slide over the screw head. The slots in the sleeve allow for the end of the sleeve to flare out radially from the centerline and the stiffness/elasticity of the material causes the sleeve to return to its original shape. The machining dimensions for the sleeve and driver shaft are designed such that the sleeve material remains slightly displaced outward by the screwhead when bottomed on the step on the shaft. This yields an axial and radial force that retains the screw to the driver shaft.

Figures 6A, 6B:
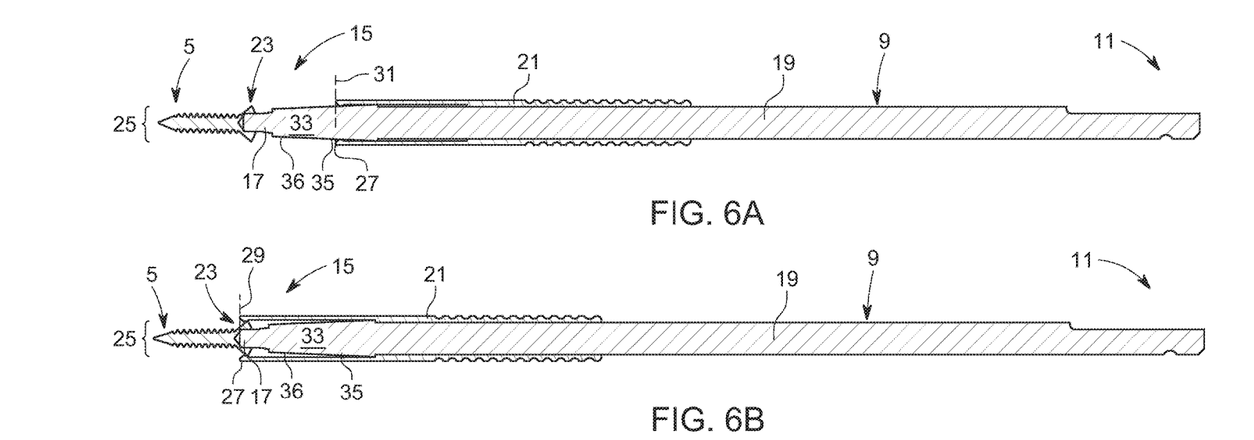
FIGS. 6A-6D are schematics illustrating in more detail the engagement of the screw retainer to the screw head.

Referring now to FIGS. 6A-6D, what are shown are section elevation views of configurations of an exemplary screwdriver 9 embodiment of the present invention with a screw 5, which are similar to the views of the embodiment shown in FIGS. 5A-C. The slots 51 of FIGS. 5A-C are not visible in these section views, at this scale. FIG. 6A is comparable to FIG. 5B. FIG. 6B is comparable to FIG. 5C, except that the section view of shows how axial end 27 extends beyond the periphery 25 when the screw retainer sleeve 21 is in the first position 29.

Figure 6C:
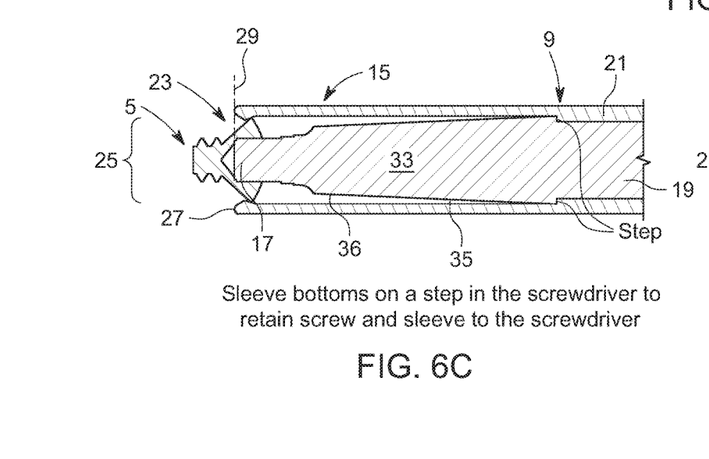

Referring now to FIG. 6C, what is shown is a closer section view of the components which are proximate the distal end 15 in FIG. 6B. Here, though, it can be seen that there is a step in the shaft 19. The sleeve 21 bottoms on the step in the shaft 19 of the screwdriver 9, to retain the screw 5 and the sleeve 21 to the screwdriver 9. Specifically, the step is sized to prevent the screw retainer sleeve 21 from translating any further toward the distal end 15 than would allow the sleeve 21 to longitudinally engage and retain the screw head 23, nor any further than would allow the axial end 27 to extend beyond the periphery 25 at the first position 29.

Figure 6D:
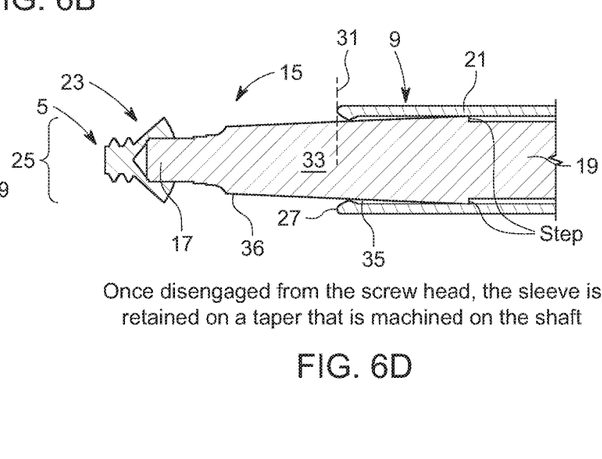

Referring now to FIG. 6D, what is shown is a closer section view of the components which are proximate the distal end 15 in FIG. 6A. Here, though, it can be more easily seen that once the sleeve 21 is disengaged from the screw head 23, the sleeve 21 is retained on a tapering section 33 that is machined on the shaft 19, because the close view makes more apparent the geometry of the axial end 27's engagement in the vicinity of a sufficiently large diameter 35 that fits the sleeve 21 well enough so as to arrest the translation of the sleeve's 21 disengagement, and engage the sleeve 21 against translating further along the shaft 19, and thereby retain it at the second position 31.

Figure 7:
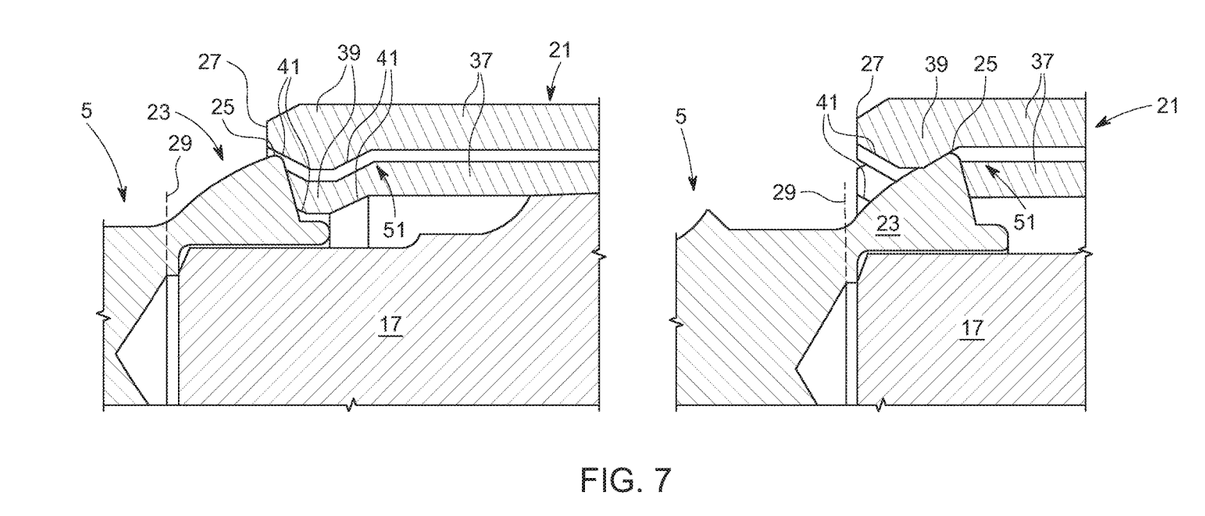
FIG. 7 is a schematic showing cross sectional views illustrating the screw retainer engaging and holding a periphery of a screw head prior to the screw being driven into the surgical fixture.

Referring now to FIG. 7, what is shown is the mechanism of engagement (and reverse order of the mechanism of disengagement) for an exemplary embodiment of a screw retainer sleeve 21, one similar to that of FIGS. 1-6. Here, the driver 17 is shown engaged with the screw head 23 of a screw 5. The screw retainer 21 comprises cantilever members 37 formed by slots 51 applied to the axial end 27. The members 37 comprise radial projections 39, which decrease the radius of the sleeve 21 proximate to the axial end 27. The screw head 23 comprises a periphery 25, the projections 39 and periphery 25 being specified to a relative size that the cantilever members 37 are adapted to bend radially outward as the contoured projections 41 of the radial projections 39 come into contact with the screw head 23, and cause the sleeve to increase in radius enough for the radial projections 39 to pass over the periphery 25 and cover the screw head 23, retaining the screw head 23 longitudinally.

Figure 8:
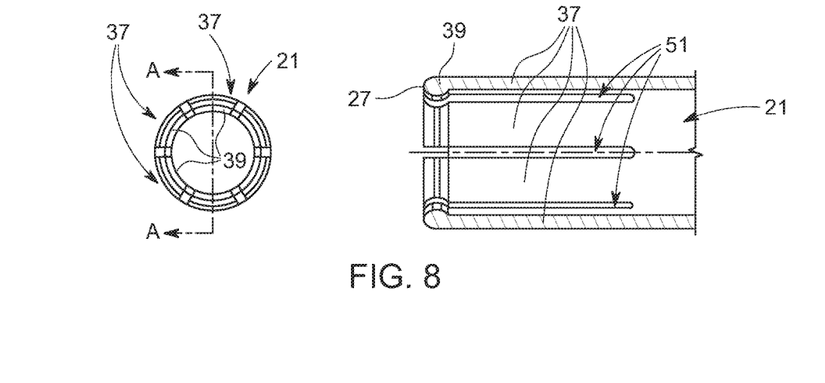
FIG. 8 is a schematic showing the arrangement of slots on a sleeve of the screw retainer.

Referring now to FIG. 8, what is shown are axial end section elevation views of a exemplary screw retainer sleeve 21 embodiment of the present invention, one that is similar to that shown in FIGS. 6A-D and FIG. 7. Here, the screw retainer sleeve 21 has slots 51 spaced at intervals about its circumference at the axial end 27, defining cantilever members 37. It also comprises radial projections 39.

By spring effect, the sleeve returning to its original shape forces the sleeve away from the screw and up the shaft toward the upper position. As the screw is driven through the cervical plate into bone, the sleeve will come into contact with the plate. Further advancing the screw forces the sleeve to move up the driver shaft away from the screw head and causes the sleeve to flare out over the screw head to disengage.

Once the flared inner diameter of the sleeve has moved passed the outer diameter of the screw head, the sleeve returns to its original shape. As the sleeve returns to its original shape the angle cut in the sleeve contacts the outer diameter of the screw head, resulting in a force that accelerates and moves the sleeve further away from the screw.

Figure 9A:
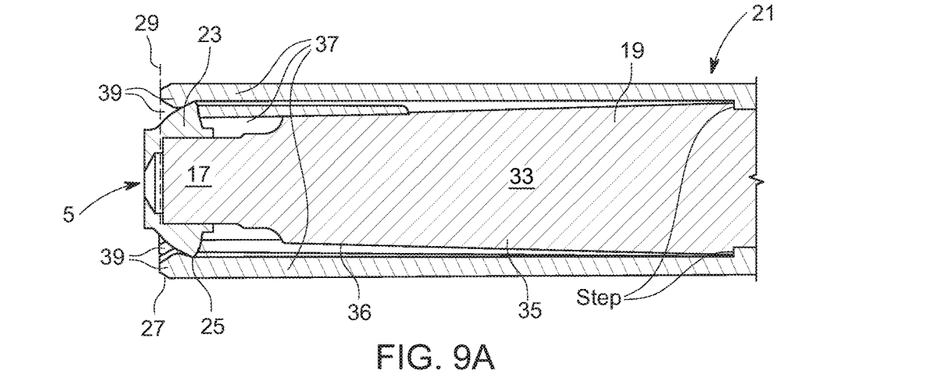
FIGS. 9A-9B are schematics similar to FIG. 7 but illustrating the screw retainer disengaging from screw head.
Figure 9B:
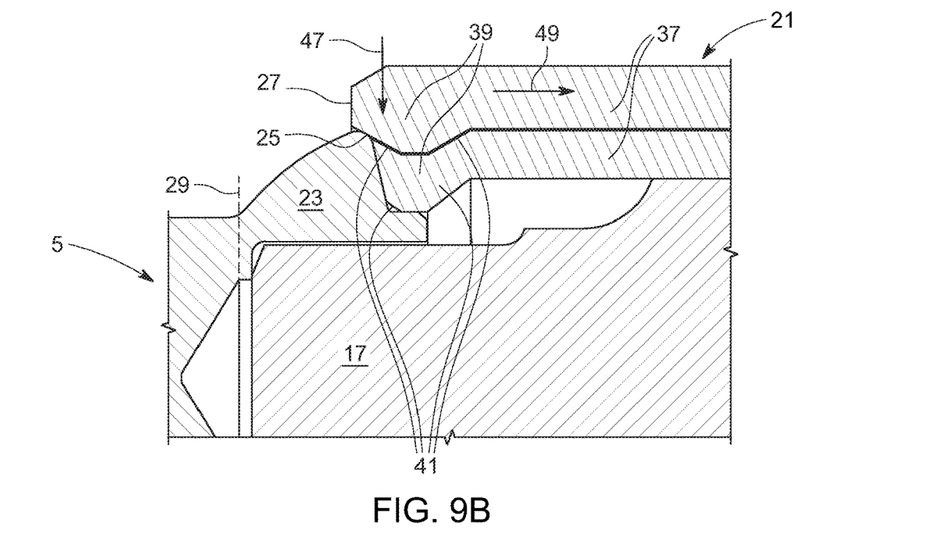
Figure 10:
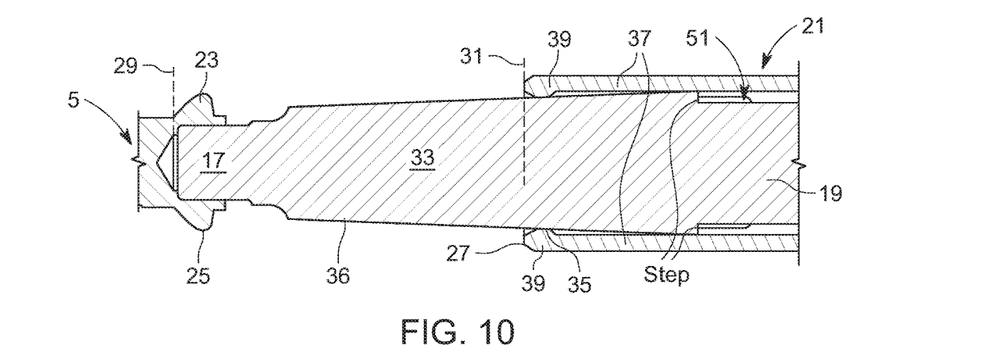
FIG. 10 is a schematic showing the screw retainer translated away from the distal end and toward the proximal end of the screw driver.

Referring now to FIGS. 9A-B and 10, what is shown are close perspective section views of an exemplary screwdriver 9 embodiment of the present invention with a screw 5. FIG. 9A is very similar to FIG. 6C, and FIG. 10 is very similar to FIG. 6D, but the closer perspectives allows embellishment of 6C by showing that it is adapted to comprise slots 51 at the axial end 27 to define cantilever members 37, and that the cantilever members also comprise radial projections 39.

With respect to FIG. 9B, what is shown is the mechanism of disengagement for an exemplary embodiment of a screw retainer sleeve 21, in the reverse manner of FIG. 7. In FIG. 9B, the sleeve 21 is shown as the radial projections 39 in contact with the screw head 23 after having passed over the periphery 25. Here, the radially bending members 37 are in contact with the screw head at their contoured projections 41. The members 37 are in a "spring back" behavior, there being a generation of a translation force 47 as the sleeve 21 returns from a biased to an unbiased state (see FIG. 12), which produces a translation force 49. The translation force 49 allows this embodiment to move without assistance between the first position 29 (FIGS. 9A, 10) to the second position 31 (FIG. 10).

With respect to FIGS. 9A-B: One important aspect of the invention is that the sleeve disengages automatically from the screw as the screw is advanced into the plate and retaining itself on the taper machined on the shaft. Conventionally, screwdrivers retain the screw to the driver. To accomplish this aspect, a taper is machined on the shaft. The shallow angle of the taper is selected such that the sleeve is slightly flared when it stops advance up the shaft and the friction between the shaft and sleeve is sufficient to hold the sleeve in place on the shaft.

As can be understood by one skilled in the art, the screw driver device and/or any of its components may have any size, shape, length, thickness, height, weight, or any other parameters. Such parameters may be selected by the surgeon (or other qualified professional) for performance of specific procedures. Further, the spinal instrument 100 and the retention mechanism 140 and/or any of its components may be manufactured from metal, plastic, synthetic material, or other suitable materials, or any combination thereof. Preferably, the spinal instrument 100 and the retention mechanism 140 are formed from titanium or stainless steel or other alloys. Alternatively, the spinal instrument 100 and the retention mechanism 140 are formed from Polyether ether ketone (PEEK), which is a colorless organic polymer thermoplastic.

Implementation Procedures

In one embodiment of the invention, there is provided a method of driving a screw with a screwdriver and a screw retainer.

Figure 11:
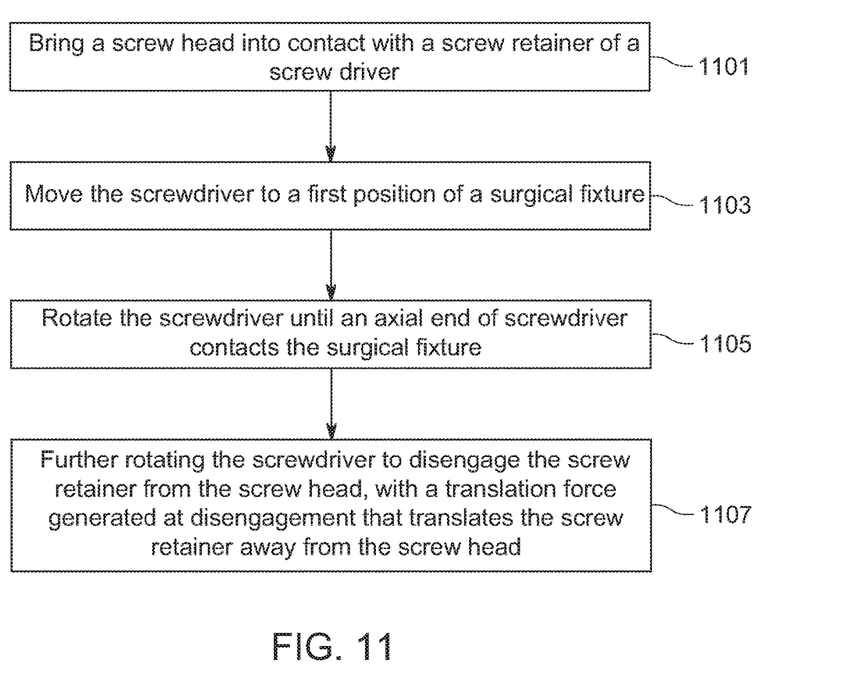
FIG. 11 is a flowchart depicting a method of the invention for driving a screw with the surgical screw driving device.

Referring now to FIG. 11, what is shown is a series of steps for carrying out such an embodiment: Bring a screw head into contact with a screw retainer of a screw driver (1101), Move the screwdriver to a first position of a surgical fixture (1103), rotate the screwdriver until axial end of screwdriver contacts the surgical fixture (1105), and further rotate the screwdriver to disengage the screw retainer from the screw head, with a translation force generated at disengagement that translates the screw retainer away from the screw head (1107).

In another embodiment of the invention, there is provided another method of driving a screw with a screwdriver and the screw retainer.

The screwdriver and the screw retainer retain the screw, and bring the screw to the plate. Then, rotating the driver advances the screw into the plate, until the screw is advanced far enough that the sleeve comes in contact with the plate. After making contact with the plate, for the rotation of the driver slips the tooth-lip-periphery of the sleeve free of the periphery of the head of the screw. The sleeve that retracts away from the driver bit/head, and is retained at a retracted position away from the head of the screw. After retainment of the sleeve away from the bit, there is an unobstructed view of the engagement of the bit with the head of the screw. The screw may be further tightened until fully seated at this point, and there is no interaction of any components that prevents removal of the driver from the screw.

Referring now to FIGS. 12A-F, what is shown is another embodiment of the invention, another method of driving a screw with a screwdriver similar to that shown in FIGS. 1-10. In all of FIGS. 12A-F, there are shown a screw 5 being driven into a surgical fixture 7, a screw retainer sleeve 21, axial end 27, and first position 29, providing the reference for the relative positions of axial end 27 as the screw 5 is driven into the fixture 7.

Referring now to FIG. 12 A, the axial end 27 has come into contact with the fixture 7. The device comprises cantilever bending members 37, comprising contoured radial protrusions 41 which are engaged with the screw head periphery 25, the screw retainer sleeve 21 being in an unstressed geometry 45. Here, the sleeve 21 is in the first position 29, and in a position of slight compression, but still drivable contact, with the fixture 7. The combined contact with the fixture 7 and with the screw head periphery 25 effects generation of a force 47. This force has a net tendency to bias the members 37 in the direction of translating radially outward.

Referring now to FIG. 12 B, the screw 5 has been driven further than in FIG. 12 A, while the axial end 27 remains in contact with the fixture 7. The cantilever members 37 shown in FIG. 12B can be considered to include radially deflected members 55, caused by radial protrusions 39 now directly sitting circumferentially about the periphery 25, thereby placing the sleeve 21 into a bent, biased state 43.

Referring now to FIG. 12 C, the screw 5 has been driven further, and the radial protrusions 39 have slipped off of the screw head periphery 25 such that the axial end 27 is no longer in contact with the fixture 7. The sleeve 21 is in a partially bent, biased state 43, with radially deflected members 55. The contoured projections 41 are now in contact with the screw 5 above the periphery 25, allowing the generation of a translating force translation force 49 which translates the screw retainer sleeve 21 away from the screw 5 and fixture 7.

Figure 12A:
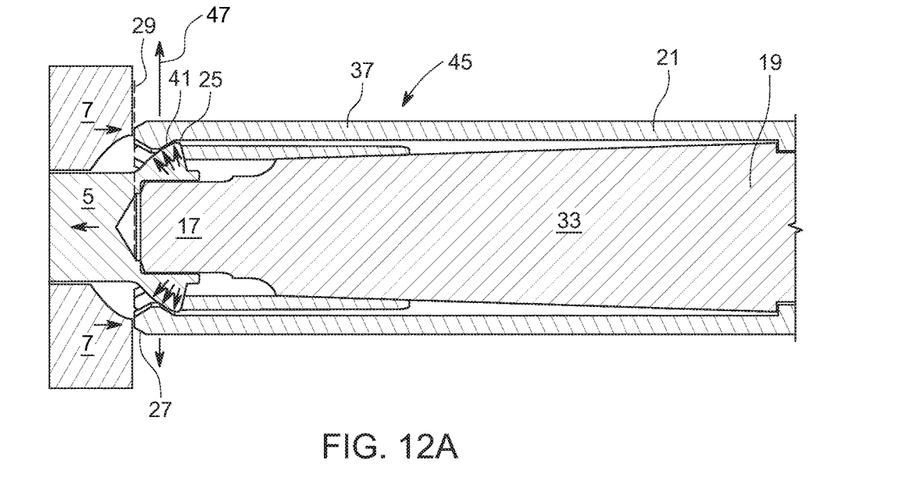
FIGS. 12A-12F are schematics illustrating a sequence by which the screw retainer moves out of a line sight to the screwhead permitting a surgeon to tighten the screw with sight on the screw and later remove the surgical screw driving device.
Figure 12B:
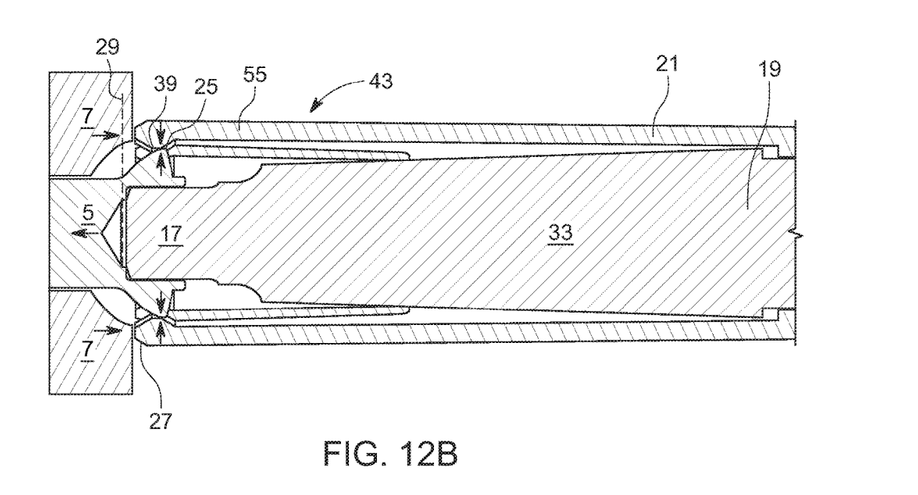
Figure 12C:
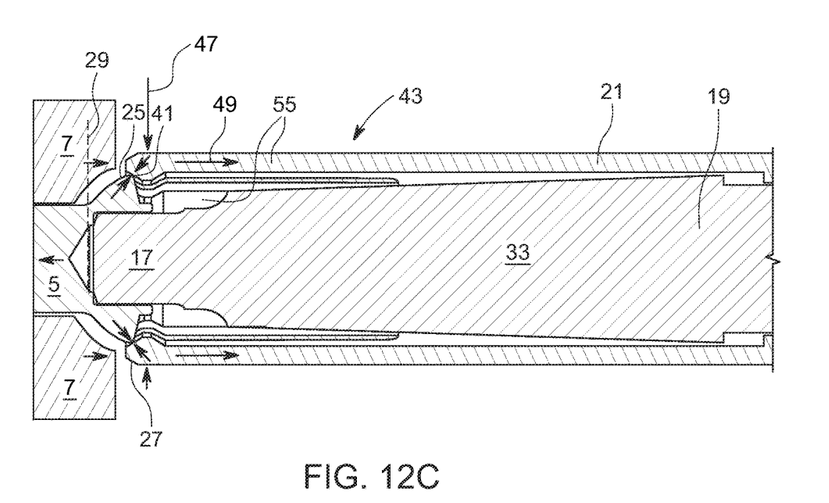
Figure 12D:
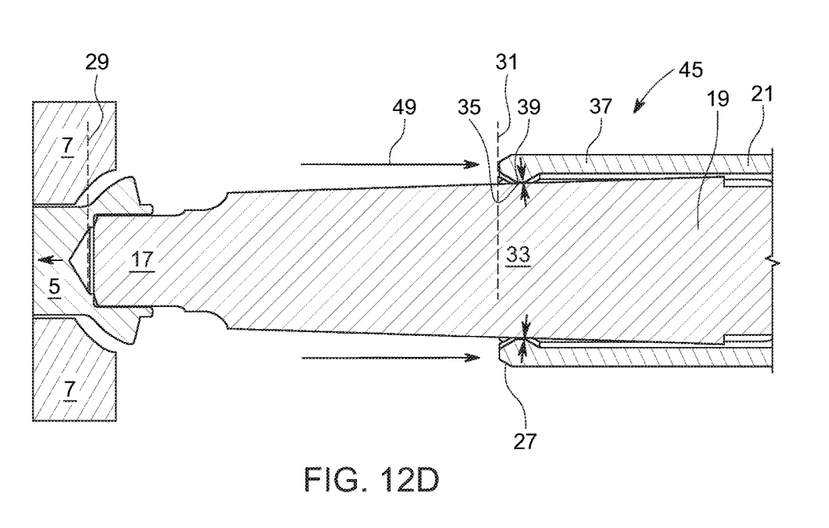

Referring now to FIG. 12D, the screw retainer sleeve 21 has translated in response to the translation force 49, and reached a second position 31. In this position 31, the radial projections 39 have come into contact with a sufficiently large diameter 35 that the screw retainer sleeve 21 has engaged a tapered section 33 and become retained against further movement.

Figure 12E:
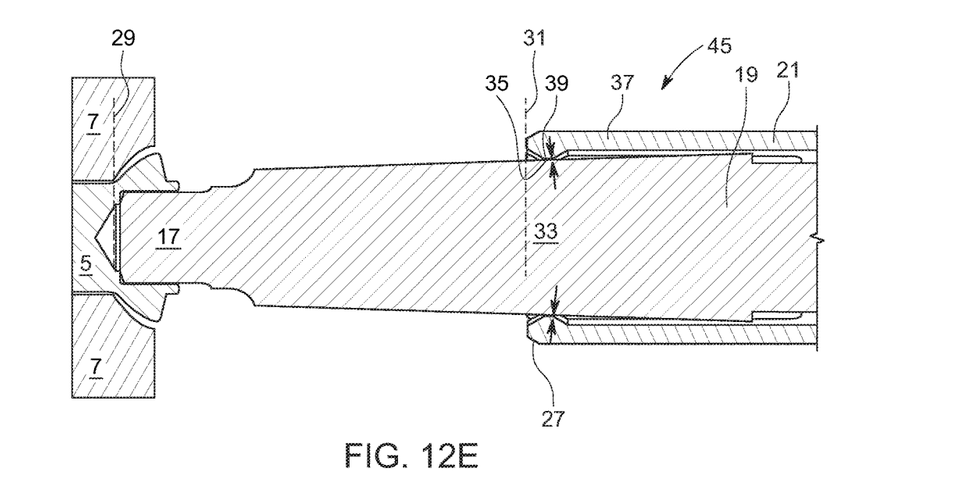
Figure 12F:
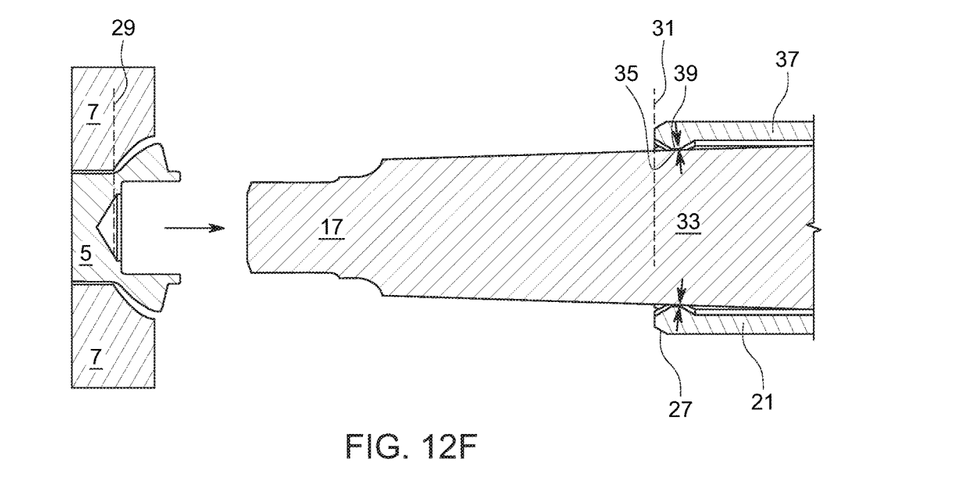

Referring now to FIG. 12E, the sleeve 21 is retained at second position 31, and the screw 5 has been driven far enough into the fixture 7 as to seat the screw 5. In FIG. 12F, the driver 17 is disengaged by linear translation away from the screw 5.

Numerous modifications and variations of the invention are possible in light of the above teachings. It is therefore to be understood that within the scope of the appended claims, the invention may be practiced otherwise than as specifically described herein.

The invention claimed is:

1. A surgical screw driving device comprising:
a screwdriver having a proximal end, a distal end having a driver for engaging a screw to be driven into a surgical fixture, and an elongated shaft extending therebetween; and
a screw retainer surrounding and extending along the elongated shaft, and configured to engage and hold a periphery of a screw head prior to the screw being driven into the surgical fixture, wherein the elongated shaft comprises a tapered section having a larger diameter section closer to the proximal end than the distal end;
wherein the screw retainer is configured to disengage from the periphery of the screw head as an axial end of the screw retainer contacts the surgical fixture, and
wherein the screw retainer comprises a slotted sleeve having cantilever members which expand over the periphery of the screw head to provide a spring force which is further configured, upon disengagement and without necessity of outside assistance, translates the screw retainer along the elongated shaft, the cantilever members contact the elongated shaft and translate along the tapered section to the larger diameter section of the screwdriver away from the distal end and toward the proximal end.

2. The device of claim 1, wherein:
the screw retainer is configured to be alternately retained at one of a first and a second position;
the first position being a position proximate the distal end where both the screw retainer is engaged with the screw head and the screw is engaged with the driver; and
the second position being a position closer to the proximal end than the distal end.

3. The device of claim 2, wherein, after disengagement of the screw head, the axial end of the screw retainer closest to the driver contacts the elongated shaft as the screw retainer translates along the elongated shaft to the second position.

4. The device of claim 3, wherein the axial end of the screw retainer comprises cantilever members extending longitudinally and have radial projections for contacting either the screw head or the elongated shaft.

5. The device of claim 4, wherein the screw retainer is configured to disengage from the screw head by translation of the cantilever members radially away from the elongated shaft as the screw retainer moves away from said first position.

6. The device of claim 5, wherein:
the radial projections remain engaged with the elongated shaft after translation of the screw retainer to the second position; and
the radial projections comprise respective contoured projections engaging the screw head.

7. The device of claim 6, wherein a translation force is generated when the radial projections disengage from the screw head by biasing of the contoured projections against the screw head.

8. The device of claim 7, wherein the translation force imparts a force on the screw retainer to move the screw retainer toward the second position.

9. The device of claim 1, wherein:
the axial end of the screw retainer comprises cantilever members extending longitudinally and have radial projections for contacting either the screw head or the elongated shaft; and
the cantilever members in engaging the screw head expand to a biased, bent geometry and return to an unbiased, unbent state to engage the screw head; and
the cantilever members in disengaging the screw head expand to a biased, bent geometry and return to an unbiased, unbent state with generation of a translation force which imparts a force on the screw retainer to move the screw retainer toward the second position.

10. The device of claim 9, the cantilever members comprise slots formed in the axial end of the screw retainer.

11. The device of claim 1, wherein the screw retainer comprises a sleeve.

12. The device of claim 1, the screw retainer comprising at least one radial projection.

13. The device of claim 12, the at least one radial projection comprises plural radial projections arranged about a circumference at the axial end of the screw retainer.

14. The device of claim 13, wherein, during engagement of the axial end of the screw retainer with the screw head, the plural radial projections are configured to extend radially outward and then contract inwardly to retain the screw head.

15. The device of claim 1, wherein:
the slotted sleeve comprising slots arranged at intervals about a circumference of the slotted sleeve.

16. A method of driving a screw with the surgical screw driving device of claim 1, the method comprising:
bringing screw head of the screw into contact with the screw retainer of claim 1, such that the screwdriver becomes engaged with the screw head;
moving the screwdriver to a first site of the surgical fixture, such that the screwdriver delivers the screw into drivable contact with the first site;
rotating the screwdriver, such that the driver at the distal end of the screwdriver drives the screw until the axial end of the screw retainer comes into contact with the surgical fixture; and
further rotating the driver after contact to disengage the screw retainer from the screw head, wherein a translation force is generated by the screw retainer upon disengagement which translates the screw retainer away from the screw head.

17. The method of claim 16, further comprising:
with the translation force and without necessity of outside assistance, translating the screw retainer to a second position which provides line of sight to the screw in the surgical fixture; and
thereafter, rotating driver until the screw is seated into the surgical fixture.

18. The method of claim 17, further comprising:
moving the screwdriver from the first site to a second site of the surgical fixture, the second site having a rotational fastener comprising at least one of a second screw or a screw lock;
bringing the driver of the screwdriver into contact with the fastener;
rotating the driver, such that the driver rotates the rotational fastener; and
moving the screwdriver away from the second site.

19. A surgical kit comprising:
at least one screw;
at least one surgical fixture;
the screwdriver of claim 1; and
a handle for coupling to the proximal end of the screwdriver clear of the screw retainer.

\* \* \* \* \*